United States Patent
Stadler et al.

[11] Patent Number: 6,090,415
[45] Date of Patent: Jul. 18, 2000

[54] PESTICIDE CONTAINING A COMBINATION OF A SPRAYED GRANULATED SULPHUR AND A PYRETHROID

[75] Inventors: Reinhold Stadler, Kirrweiler; Reiner Kober, Fussgönheim; Karl-Heinrich Schneider, Kleinkarlbach; Volker Harries, Frankenthal; Egon Weinmüller, Limburgerhof; Eberhard Kleinbach, Ludwigshafen; Adolf Parg, Bad Dürkheim; Jörn Tidow, Schwetzingen; Ulrich Bröckel, Freinsheim, all of Germany; Ulrich Meier, Lorena Sp; Cleide M. C. Marques Oliveira, Sao Paulo, both of Brazil; Karl-Friedrich Jäger, Limburgehof; Ulrich Kiessling, Erpolzheim, both of Germany

[73] Assignee: BASF Aktiengesellschaft, Ludwigshafen, Germany

[21] Appl. No.: 09/043,315
[22] PCT Filed: Sep. 13, 1996
[86] PCT No.: PCT/EP96/04026
  § 371 Date: Mar. 17, 1998
  § 102(e) Date: Mar. 17, 1998
[87] PCT Pub. No.: WO97/10715
  PCT Pub. Date: Mar. 27, 1997

[30] Foreign Application Priority Data

Sep. 23, 1995 [DE] Germany .......... 195 35 403

[51] Int. Cl.$^7$ .......... A01N 59/02; A01N 53/00; A01N 53/02; A01N 53/06; A01N 25/14
[52] U.S. Cl. .......... 424/713; 424/703; 424/705; 424/714; 424/409; 424/417; 424/489; 424/490; 514/521; 514/522; 514/531; 514/721; 514/951; 514/952; 504/119
[58] Field of Search .......... 424/703, 705, 424/713–714, 409, 417, 489, 490; 504/119; 514/521, 522, 531, 721, 951, 952

[56] References Cited

U.S. PATENT DOCUMENTS 5,788,896  8/1998  Bertram et al. .......... 264/8

FOREIGN PATENT DOCUMENTS

| | | |
|---|---|---|
| 2545325 | 11/1984 | France . |
| 2589325 | 5/1987 | France . |
| 2185005 | 7/1987 | United Kingdom . |
| 82/03216 | 6/1987 | WIPO . |

OTHER PUBLICATIONS

The Pesticide manual, 10$^{th}$ Ed. pp. 260, 288 (1994).

*Primary Examiner*—John Pak
*Attorney, Agent, or Firm*—Keil & Weinkauf

[57] ABSTRACT

The present invention relates to pesticides which comprise an active ingredient combination composed of
  a) sulfur spray granules and
  b) a pyrethroid, and to processes for the preparation of these pesticides.

17 Claims, No Drawings

PESTICIDE CONTAINING A COMBINATION OF A SPRAYED GRANULATED SULPHUR AND A PYRETHROID

This application is a 371 of PCT/EP96/04026, filed on Sep. 13, 1996.

The present invention relates to pesticides which comprise an active ingredient combination composed of a) sulfur spray granules and b) a pyrethroid, and to processes for the preparation of these pesticides.

It has been disclosed to use sulfur as a pesticide, mainly as a fungicide, but also, for example, as an acaricide. It has furthermore been disclosed to use pyrethroids as insecticides and acaricides. It has furthermore been disclosed to employ sulfur as a pesticide in combination with an insecticide, eg. parathion-methyl, or a pyrethroid, such as cypermethrin or deltamethrin (The Pesticide Manual, 10th Edition, p. 934, p. 260, p.288).

However, the prior-art compositions and their formulations are not yet satisfactory since in some cases their crop protection action is insufficient, or because their formulation, eg. a wettable powder, may result in a hazard to the user, eg. skin irritations, due to the danger of dust formation, or because the dispersibility of such powders is poor and can result in lump formation in the spray tanks.

It is an object of the present invention to find mixtures and formulations with which pests such as insects or arachnids can be controlled more advantageously and which additionally show advantages upon use on the basis of their formulation and which have an improved activity against pests combined with a reduced total amount of active ingredient applied (synergistic mixture).

We have found that this object is achieved by the compositions defined at the outset. It has furthermore been found that better control of the pests is possible by using the active ingredient combination of a) and b) than with the individual compounds.

The pesticides according to the invention are suitable for effecting efficient control of pests, in particular from the classes of the insects and arachnids. The compositions according to the invention are applied particularly advantageously for controlling pests which are little exposed to customary spray applications due to their habit of mainly occurring in poorly accessible locations, such as along the archis of leaves or in primordial buds, flowers, fruit and leaves before their development, so that the activity of the conventionally employed insecticides is frequently only insufficient. In contrast, the pesticides according to the invention have a flushing effect on these hiding target pests and thus on their increased exposure, which results in more successful control.

Component a) for the pesticides according to the invention is formed by sulfur spray granules. In general, sulfur melt spray granules and sulfur spray granules made of suspended sulfur are used as sulfur spray granules.

Sulfur melt spray granules are obtained for example by melting elemental sulfur, eg. sulfur powder, by heating to temperatures of above 120° C. and spraying the resulting melt in a suitable spraying apparatus, eg. a spray tower, if desired after adding wetting agents and dispersants, generally with cooling, to form the sulfur spray granules.

Examples of wetting agents and dispersants are:

fatty acid polyoxyethylene esters, such as lauryl alcohol polyoxyethylene ether acetate, alkylpolyoxyethylene ethers or alkylpolyoxypropylene ethers, for example of isotridecyl alcohol and fatty alcohol polyoxyethylene ether, alkylaryl alcohol polyoxyethylene ethers, such as octylphenyl polyoxyethylene ether, tributylphenyl polyoxyethylene ether, ethoxylated iso-octylphenol, octylphenol, nonylphenol or castor oil, sorbitol esters, arylsulfonic acids, alkylsulfonic acids, alkylsulfuric acids, alkali metal, alkaline earth metal and ammonium salts of arylsulfonic acids, eg. ligno-, phenol-, naphthalene- and dibutylnaphthalenesulfonic acids, alkylsulfonic acids, alkylarylsulfonic acids, alkylsulfuric acids, lauryl ether sulfonic acids and fatty alcohol sulfuric acids, fatty acids, sulfated hexa-, hepta- and octadecanols and fatty alcohol glycol ethers, condensates of sulfonated naphthalene and its derivatives with formaldehyde, condensates of naphthalenesulfonic acids with phenol and formaldehyde, protein hydrolysates and in particular as dispersants: lignosulfite waste liquors and methylcellulose.

Sulfur spray granules of suspended sulfur are obtained for example in such a way that a sulfur suspension is first prepared, expediently in such a way that elemental sulfur, eg. sulfur powder, is suspended in water, expediently with an addition of wetting agents and dispersants with or without the addition of a binder. The sulfur suspension is preferably comminuted in ball mills or stirred ball mills using a grinding medium, for example a grinding medium made of glass or other mineral or metallic grinding medium, in a size of 0.1–30 mm, preferably 0.6–2 mm, until the average particle size is markedly below 10 $\mu$m. Suitable wetting agents and dispersants are, for example, those which have been mentioned above in the case of the sulfur melt spray granules.

Examples of suitable binders are cellulose derivatives such as cellulose esters, cellulose ethers, eg. carboxymethylcellulose, hydroxypropylmethylcellulose, water-soluble gums such as gum arabic, tragacanth gum, alginates, gelatin, polyvinylpyrrolidones, or modified starches such as sodium carboxymethyl starch.

The resulting sulfur suspension which contains typically 300–800 g/l of elemental sulfur is subsequently sprayed in a spraying apparatus, eg. in a spray tower, at from generally 80 to 120° C., to form the sulfur spray granules.

Suitable pyrethroids which are used as component b) for the pesticides according to the invention are, for example (in each case common name in accordance with The Pesticide Manual, 10th Edition): permethrin, fenvalerate, esfenvalerate, cypermethrin, alpha-cypermethrin, deltamethrin, fenpropathrin, fluvalinate, flucythrinate, cyfluthrin, acrinathrin, tralomethrin, cycloprothrin, lambda-cyhalothrin, tefluthrin, bifenthrin, transfluthrin, zeta-cypermethrin, fubfenprox, flufenprox.

The weight ratio of sulfur spray granules to pyrethroids in the pesticides according to the invention is, as a rule, 1000:0.1 to 1000:500, preferably 1000:0.1 to 1000:100, in particular 1000:0.1 to 1000:10. In general, the pesticide comprises 0.1 to 100% by weight, preferably 0.1 to 99% by weight, in particular 1 to 98% by weight, of the active ingredient combination of a) and b).

The pesticides according to the invention can be prepared in such a way that the sulfur spray granules are mixed with the pyrethroid which is fixed on an inert pulverulent carrier and exists in the form of a powder. Examples of suitable mixing apparatuses are conical screw mixers (Nauta mixers), plow-share mixers, drum mixers. Suitable inert carriers for the preparation of the pyrethroid powder formulation are, for example, silicas, alumina, silica gel, kieselguhr, talc, kaolin, clays, quartz sand, silicates such as aluminum silicates, magnesium silicates, bentonites, montmorillonites, attapulgites, zeolites. Substances which are advantageously used are highly-disperse silicas which are known, for example, under the name Sipernat®.

In general, the pyrethroid which is fixed to the carrier material is obtained in such a way that the pyrethroid, as such or as solution in an organic solvent, is sprayed onto the carrier material. Examples of suitable solvents are ketones such as acetone, ethers such as tetrahydrofuran, alcohols such as methanol, ethanol, propanols, esters such as ethyl acetate, halogenated hydrocarbons, eg. methylene chloride or 1,2-dichloroethene. The weight ratio of pyrethroid to inert carrier material is generally 0.1:100 to 10:1, preferably 0.5:100 to 1:1.

Another process for the preparation of the pesticides according to the invention consists in spraying the pyrethroid, as such or as a solution in an organic solvent, with or without further adjuvants such as wetting agents and binders, onto the sulfur spray granules which are first introduced, for example in a fluidized bed.

Examples of useful solvents for the pyrethroids are ketones such as acetone, ethers such as tetrahydrofuran, alcohols such as methanol, ethanol, propanols, esters such as ethyl acetate, halogenated hydrocarbons, eg. methylene chloride or 1,2-dichloroethene.

Examples of suitable wetting agents are:

Polyoxyethylene/polyoxypropylene block copolymers, for example those disclosed in U.S. Pat. No. 2,677,700, U.S. Pat. No. 2,674,619 and EP-A 298 909; especially suitable products of this group are commercially available for example under the name PLURONIC® (BASF Wyandotte Corp.), for example PLURONIC® PE 3100, PE 6100 and PE 8100).

Polyoxyethylene or polyoxyethylene/polyoxypropylene fatty alcohols, for example those disclosed in GB-A 643 422 or Satkowski et al., Ind. Eng. Chem. 49 (1957) 1875; especially suitable products of this group are commercially available for example under the name WETTOL®LF (BASF).

Polyoxyethylene or polyoxyethylene/polyoxypropylene fatty amines, for example those described in Stache, Tensidtaschenbuch [Surfactants Guide], Carl Hauser-Verlag Munich, Vienna, 2nd Edition, p. 133; especially suitable products of this group are commercially available for example under the names ATPLUS® (Atlas) and Ethomeen® (Akzo).

Fatty acid esters or fatty acid ester ethoxylates, for example those disclosed in U.S. Pat. No. 1,914,100; especially suitable products of this group are commercially available for example under the names ARLACEL®, ATMER®, ATMOS® and ATPET® (Atlas).

Polyoxyethylene or polyoxyethylene/polyoxypropylene oxyalcohols, for example disclosed in U.S. Pat. No. 2,508,035, U.S. Pat. No. 2,508,036, U.S. Pat. No. 2,617,830; especially suitable products of this group are commercially available for example under the name LUTENSOL AO® and LUTENSOL TO® (BASF).

Polyoxyethylene or polyoxyethylene/polyoxypropylene alkylphenols, for example those disclosed in FR-A 842 943; especially suitable products of this group are commercially available for example under the name LUTENSOL AP® (BASF).

Examples of suitable binders are cellulose derivatives such as cellulose esters, cellulose ethers, for example carboxymethylcellulose, hydroxypropylmethylcellulose, water-soluble gums such as gum arabic, gum tragacanth, alginates, gelatin, polyvinylpyrrolidones, modified starches such as sodium carboxymethyl starch.

The pesticides according to the invention can furthermore be prepared in such a way that pyrethroid, in the form of an emulsion, is sprayed on the sulfur spray granules, it being possible for the emulsion to comprise, besides emulsifiers, other adjuvants such as wetting agents and binders. Examples of suitable wetting agents and binders are those which have already been mentioned above. Examples of suitable emulsifiers are:

fatty acid polyoxyethylene esters, such as lauryl alcohol polyoxyethylene ether acetate, alkylpolyoxyethylene ethers or alkylpolyoxypropylene ethers, for example of isotridecyl alcohol and fatty alcohol polyoxyethylene ether, alkylaryl alcohol polyoxyethylene ethers, such as octylphenyl polyoxyethylene ether, tributylphenyl polyoxyethylene ether, ethoxylated iso-octylphenol, octylphenol, nonylphenol or castor oil, sorbitol esters, arylsulfonic acids, alkylsulfonic acids, alkylsulfuric acids, alkali metal, alkaline earth metal and ammonium salts of arylsulfonic acids, eg. ligno-, phenol-, naphthalene- and dibutylnaphthalenesulfonic acids, alkylsulfonic acids, alkylarylsulfonic acids, alkylsulfuric acids, lauryl ether sulfonic acids and fatty alcohol sulfuric acids, fatty acids, sulfated hexa-, hepta- and octadecanols and fatty alcohol glycol ethers, condensates of sulfonated naphthalene and its derivatives with formaldehyde, condensates of naphthalenesulfonic acids with phenol and formaldehyde and, protein hydrolysates.

The pesticides according to the invention can furthermore be obtained immediately when preparing the sulfur spray granules in such a manner that, when the sulfur melt spray granules are prepared, the pyrethroid is metered to the sulfur melt before spraying it to produce the melt spray granules, or that, when the sulfur spray granules are prepared from suspended sulfur, the suspended sulfur together with the pyrethroid, for example in suspended form or in the above-described pyrethroid powder formulation, which has been obtained using a carrier, is sprayed to produce the spray granules.

Due to their formulation, the pesticides according to the invention have a very good dispersion behavior when applied by spraying, and a very good storage stability with no signs of separation, and no caking even after thermal stress.

The pesticides according to the invention are suitable for the efficient control of pests from the classes of the insects and arachnids. They can be employed as pesticides in crop protection and in the hygiene, stored product and veterinary sector, the use in crop protection and in the veterinary sector being preferred.

The harmful insects include:

from the order of the lepidopterans (Lepidoptera), for example, *Adoxophyes orana, Agrotis ypsilon, Agrotis segetum, Alabama argillacea, Anticarsia gemmatalis, Argyresthia conjugella, Autographa gamma, Cacoecia* murinana, Capua reticulana, Choristoneura fumiferana, Chilo partellus, Choristoneura occidentalis, Cirphis unipuncta, Cnaphalocrocis medinalis, Crocidolomia binotalis, Cydia pomonella, Dendrolimus pini, Diaphania nitidalis, Diatraea grandiosella, Earias insulana, Elasmopalpus lignosellus, Eupoecilia ambiguella, Feltia subterranea, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera scitella, Lithocolletis blancardella, Lobesia botrana, Loxostege sticticalis, Lymantria dispar, Lymantria monacha, Lyonetia clerkella, Manduca sexta, Malacosoma neustria, Mamestra brassicae, Mocis repanda, Operophthera brumata, Orgyia pseudotsugata, Ostrinia nubilalis, Pandemis heparana, Panolis flammea, Pectinophora gossypiella, Phthorimaea operculella, Phyllocnistis citrella, Pieris brassicae, Plathypena scabra, Platynota stultana, Plutella xylostella, Prays citri, Prays oleae, Prodenia sunia, Prodenia ornithogalli, Pseudoplusia includens, Rhyacionia frustrana, Scrobipalpula absoluta, Sesamia inferens, Sparganothis pilleriana, Spodoptera frugiperda, Spodoptera littoralis, Spodoptera litura, Syllepta derogata, Synanthedon myopaeformis, Thaumatopoea pityocampa, Tortrix viridana, Trichoplusia ni, Tryporyza incertulas, Zeiraphera canadensis, furthermore Galleria mellonella and Sitotroga cerealella, Ephestia cautella, Tineola bisselliella;

from the order of the beetles (Coleoptera), for example, Anthonomus grandis, Anthonomus pomorum, Apion vorax, Atomaria linearis, Blastophagus piniperda, Cassida nebulosa, Cerotoma trifurcata, Ceuthorhynchus assimilis, Ceuthorhynchus napi, Chaetocnema tibialis, Conoderus vespertinus, Crioceris asparagi, Dendroctonus refipennis, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllopertha horticola, Phyllophaga sp., Phyllotreta chrysocephala, Phyllotreta nemorum, Phyllotreta striolata, Popillia japonica, Psylliodes napi, Scolytus intricatus, Sitona lineatus, furthermore Bruchus rufimanus, Bruchus pisorum, Bruchus lentis, Sitophilus granaria, Lasioderma serricorne, Oryzaephilus surinamensis, Rhyzopertha dominica, Sitophilus oryzae, Tribolium castaneum, Trogoderma granarium, Zabrotes subfasciatus;

from the order of the dipterans (Diptera), for example, Anastrepha ludens, Ceratitis capitata, Contarinia sorghicola, Dacus cucurbitae, Dacus oleae, Dasineura brassicae, Delia coarctata, Delia radicum, Hydrellia griseola, Hylemyia platura, Liriomyza sativae, Liriomyza trifolii, Mayetiola destructor, Orseolia oryzae, Oscinella frit, Pegomya hyoscyami, Phorbia antiqua, Phorbia brassicae, Phorbia coarctata, Rhagoletis cerasi, Rhagoletis pomonella, furthermore Aedes aegypti, Aedes vexans, Anopheles maculipennis, Chrysomya bezziana, Chrysomya hominivorax, Chrysomya macellaria, Cordylobia anthropophaga, Culex pipiens, Fannia canicularis, Gasterophilus intestinalis, Glossina morsitans, Haematobia irritans, Haplodiplosis equestris, Hypoderma lineata, Lucilia caprina, Lucilia cuprina, Lucilia sericata, Musca domestica, Muscina stabulans, Oestrus ovis, Tabanus bovinus, Simulium damnosum;

from the order of the thripse (Thysanoptera), for example, Frankliniella fusca, Frankliniella occidentalis, Frankliniella tritici, Haplothrips tritici, Scirtothrips citri, Thrips oryzae, Thrips palmi, Thrips tabaci;

from the order of the hymenopterans (Hymenoptera), for example, Athalia rosae, Atta cephalotes, Atta sexdens, Atta texana, Hoplocampa minuta, Hoplocampa testudinea, Iridomyrmes humilis, Iridomyrmex purpureus, Monomorium pharaonis, Solenopsis geminata, Solenopsis invicta, Solenopsis richteri;

from the order of the heteropterans (Heteroptera), for example, Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus hesperus, Lygus lineolaris, Lygus pratensis, Nezara viridula, Piesma quadrata, Solubea insularis, Thyanta perditor;

from the order of the homopterans (Homoptera), for example, Acyrthosiphon onobrychis, Acyrthosiphon pisum, Adelges laricis, Aonidiella aurantii, Aphidula nasturtii, Aphis fabae, Aphis gossypii, Aphis pomi, Aulacorthum solani, Bemisia tabaci, Brachycaudus cardui, Brevicoryne brassicae, Dalbulus maidis, Dreyfusia nordmannianae, Dreyfusia piceae, Dysaphis radicola, Empoasca fabae, Eriosoma lanigerum, Laodelphax striatella, Macrosiphum avenae, Macrosiphum euphorbiae, Macrosiphon rosae, Megoura viciae, Metopolophium dirhodum, Myzus persicae, Myzus cerasi, Nephotettix cincticeps, Nilaparvata lugens, Perkinsiella saccharicida, Phorodon humuli, Psylla mali, Psylla piri, Psylla pyricola, Rhopalosiphum maidis, Schizaphis graminum, Sitobion avenae, Sogatella furcifera, Toxoptera citricida, Trialeurodes abutilonea, Trialeurodes vaporariorum, Viteus vitifolii;

from the order of the termites (Isoptera), for example, Calotermes flavicollis, Leucotermes flavipes, Macrotermes subhyalinus, Odontotermes formosanus, Reticulitermes lucifugus, Termes natalensis;

from the order of the orthopterans (Orthoptera), for example, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Schistocerca americana, Schistocerca peregrina, Stauronotus maroccanus, Schistocerca gregaria, furthermore Acheta domestica, Blatta orientalis, Blattella germanica, Periplaneta americana;

the class of the arachnids (Arachnoidea) include, for example, phytophagous mites (Acari), such as Aculops lycopersicae, Aculops pelekassi, Aculus schlechtendali, Brevipalpus phoenicis, Bryobia praetiosa, Eotetranychus carpini, Eutetranychus banksii, Eriophyes sheldoni, Oligonychus pratensis, Panonychus ulmi, Panonychus citri, Phyllocoptruta oleivora, Polyphagotarsonemus latus, Tarsonemus pallidus, Tetranychus cinnabarinus, Tetranychus kanzawai, Tetranchus pacificus, Tetranychus urticae, ticks, such as Amblyomma americanum, Amblyomma variegatum, Argas

*persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Rhipicephalus appendiculatus* and *Rhipicephalus evertsi*, and animal-parasitic mites, such as *Dermanyssus gallinae, Psoroptes ovis* and *Sarcoptes scabiei*.

When using the pesticides according to the invention in veterinary medicine, they are advantageously employed for controlling ectoparasites.

Under field conditions, the rate of application of the active ingredient combination for controlling pests is generally from 0.01 to 50 kg/ha, preferably 0.05 to 20 kg/ha, in particular 0.1 to 10 kg/ha.

The examples which follow illustrate the invention.

A) Formulation Examples
1. Preparation of Sulfur Spray Granules
Preparation of Sulfur Melt Spray Granules Sulfur powder is heated to above 120° C. and melted. The melt is mixed with sodium lignosulfonate as wetting agent and silica as dispersant. The melt mixture is sprayed in a spray tower using a 2-substance model. This gives readily dispersible spray granules (particle size: 60<x<300 μm), which comprises 0.3% by weight of dispersant and approximately 20% by weight of wetting agent. The remainder is sulfur.

Example B

Preparation of sulfur spray granules from suspended sulfur

Sulfur powder is suspended in water, sodium lignosulfonate is added as dispersant, and nonylphenyl ethoxylate is added as wetting agent. The suspension is brought to a pumpable concentration, ie. expediently to a sulfur concentration of 20 to 40% by weight. Based on the entire dry matter, sulfur amounts to 80% by weight, the sodium lignosulfonate in the example to a concentration of 19% and the wetting agent to a concentration of 1%. Adding an antifoam, eg. silicone at a concentration of up to 0.1%, accelerates the binding process. The batch is ground in a laboratory stirred ball mill to give a sprayable suspension. The suspension is sprayed in a spray tower in a two-substance model to give microgranules. This gives readily dispersible granules of the composition:

79–80% by weight of sulfur
19% by weight of sodium lignosulfonate
1% by weight of nonylphenol (wetting agent)
0.1% by weight of silicone 2. Preparation of an Active Ingredient Combination According to the Invention

EXAMPLE 1

In a first step, a powder formulation of the pyrethroid cypermethrin is prepared in such a way that cypermethrin is dissolved in acetone, and, in a fluidized bed, the cypermethrin solution acetone is sprayed onto silica powder as the carrier. This gives a cypermethrin/carrier powder which comprises 32.4% by weight of cypermethrin.

In a Nauta mixer, the cypermethrin/carrier powder is subsequently mixed with sulfur melt spray granules of Example A. This gives a ready mix in the form of dispersible granules which comprises 80% by weight of sulfur and 5% by weight of cypermethrin. The product is readily wettable and dissolves immediately after the addition of water giving a suspension which is stable upon processing, without any particles sedimenting.

EXAMPLE 2

Sulfur melt granules obtained as described in Example A are introduced in a fluidized bed. A solution of cypermethrin in acetone (25% by weight strength), which additionally comprises 4% by weight of a polyoxyethylene/polyoxypropylene fatty alcohol, is sprayed onto these carrier granules. A quantity of the acetone solution which comprises 100 g of cypermethrin is sprayed onto 2 kg of the sulfur spray melt granules at a spray rate of 13 g of acetone solution/minute. The sulfur melt spray granules is fluidized in an amount of air of 130 m³/h. The acetone solution is sprayed at a spray pressure of 1.5 bar. This gives readily dispersible spray granules which, together with water, give a suspension which is stable upon processing and from which no particles sediment. This process variant is of interest for cypermethrin concentrations of above approximately 5%.

Spray granules according to the invention which have been obtained as described in this Example 2 are compared with a conventional powder mixture of wettable sulfur and pyrethroid regarding the dispersant properties. The results shown in the table which follows were obtained:

| Criterion | Wettable sulfur + 0.13% of pyrethroid | Spray granules as described in Example 2 |
| --- | --- | --- |
| Dissolution | greatly delayed disintegration | rapid disintegration |
| Sediment after 30 minutes | 3.25 ml | 1.4 ml |
| Granule formation | very pronounced granule formation | slight granule formation |
| Foam formation | none | slight, rapidly disappearing foam formation |

The results show that the dispersing properties of the formulation according to the invention are markedly improved in comparison with the conventional compositions.

EXAMPLE 3 a) Elemental, finely-ground sulfur is treated with 18% by weight of sodium lignosulfonate as dispersing agent, giving a pulverulent sulfur formulation.

b) Cypermethrin/carrier powder is prepared as described in the first paragraph of Example 1.

The pulverulent components obtained above as shown under a) and b) are mixed and the mixture is suspended in water. In a spray tower, the suspension is sprayed to give sulfur spray granules which comprise 5% by weight of cypermethrin and 80% by weight of sulfur. The resulting sulfur spray granules are readily dispersible and, together with water, give a suspension which is stable upon processing and from which no particles sediment.

This variant can be employed in particular for lower concentrations of pyrethroids with a low melting temperature or for pyrethroids in the form of crystals of melting points of above 70° C. in a wide concentration range.

EXAMPLE 4

In a laboratory mixer, 40 g of deltamethrin, 15 g of formaldehyde/urea/phenolsulfonic acid condensate in the form of the sodium salt, 5 g of formaldehyde/phenolsulfonic acid condensate in the form of the sodium salt, 5 g of diisobutylnaphthalenesulfonic acid in the form of the sodium salt, 25 g of kaolin and 10 g of precipitated silica are mixed, and this mixture is ground in a laboratory high-speed rotor mill to give a water-dispersible powder (product 1).

In a second step, 987.5 g of water-dispersible granules composed of 81% of sulfur, 17% of sodium lignosulfonate and 2% of residual moisture were mixed, in a cubicle blender, with 12.5 g of product 1 for 60 minutes at a speed of 30 rpm. Homogeneous water-dispersible granules of sulfur and deltamethrin were obtained. The mixed product was readily flowable, produced little dust and dispersed rapidly and completely when introduced into water. A homogeneous dispersion with a suspendability of 93.9% (method: CIPAC MT 168) was obtained.

EXAMPLE 5

A master batch of cypermethrin and a dispersant was mixed by a method similar to Example 4. This mixture is heated to melting point and metered into a plow-share mixer into which a mixture of kaolin and precipitated silica has been introduced under a pressure of over 10 bar using a rapidly rotating disperser and a two-substance model. A masterbatch can be obtained by means of this mixture.

Following the procedure described in the above paragraph, 100 g of cypermethrin, sprayed at a rate of 10 g/minute,
40 g of condensate in the form of the sodium salt,
10 g of sodium diisobutylnaphthalenesulfonate,
50 g of kaolin and
25 g of precipitated silica are introduced into the mixer.

In a helical cone mixer, this masterbatch is mixed with sulfur granules by a method similar to Example 4.

B) Use Examples

1. Control of Leaf-feeding Caterpillars (*Spodoptera frugiperda*) in Maize (Brazil).

The tests were carried out in the open (block design with 4 replications, 80 m²/plot) with a water application rate of 200–400 l/ha.

2 hours after the treatment, an increased mobility (flushing effect) of the insects was observed in the sulfur-treated plot in comparison with untreated areas.

The results were as follows:

|  |  | % activity (mortality) | |
|---|---|---|---|
|  | Dosage product | 7 days post-treatment | 12 days post-treatment |
| β-Cyfluthrin | 0.15 1/ha | 62 | 65 |
| β-Cyfluthrin in combination with sulfur spray granules | 0.15 1/ha + 1.0 kg/ha | 88 | 85 |
| β-Cyfluthrin | 0.2 1/ha | 85 | 63 |
| β-Cyfluthrin in combination with sulfur spray granules | 0.2 1/ha + 1.0 kg/ha | 92 | 85 |
| Untreated control |  | (62)* | (71)* |

*) = % plants with caterpillar infestation

2. Control of Spider Mites (Tetranychus spp.) in Cotton, Cultivar Mahyco 8 (India)

The relevant dates of the tests were:

| Sowing date | 26.06.1994 |
|---|---|
| Treatment 1 | 01.09.1994 |
| Treatment 2 | 12.09.1994 |
| Harvesting date 1 | 14.11.1994 |
| Harvesting date 2 | 27.11.1994 |

The following results were obtained:

| Treatment | Dosage in g of active ingredient (a.i.)/ha | Total yield (kg/ha) of cotton |
|---|---|---|
| Untreated control | — | 650 |
| Cypermethrin | 60 | 962 |
| Sulfur spray granules | 625 | 700 |
| Cypermethrin in combination with sulfur spray granules | 60 625 | 1062 |

3. Control of Spider Mites (Tetranychus sp.) and Fruit Borers (Leucinodes sp.) in Aubergines (Solanum melongena)

3 treatments were carried out as follows:

| Treatment 1 | 16.12.1993 |
|---|---|
| Treatment 2 | 23.03.1994 |
| Treatment 3 | 10.06.1994 |

The following results were achieved:

|  |  | % Mortality (mites) | | |
|---|---|---|---|---|
|  | Dosage in g of a.i./ha | 3 days post-treatment | 7 days post-treatment | Relative yield |
| Untreated control | — | — | — | 100 |
| Cypermethrin | 50 | 19*) 9**) 0***) | 46*) 43**) 13***) | 160 |
| Sulfur spray granules | 625 | 55*) 57**) 60***) | 58*) 47**) 43***) | 177 |
| Cypermethrin in combination with sulfur spray granules | 50 625 | 66*) 73**) 82***) | 71*) 71**) 73***) | 185 |

*)Treatment 1
**)Treatment 2
***)Treatment 3

4. Control of spider mites (Tetranychus sp.) in Aubergines
The results were as follows:

|  |  | % activity (mortality) | | |
| --- | --- | --- | --- | --- |
| Treatment | g of a.i./ha | 1 day post-treatment | 3 days post-treatment | 7 days post-treatment |
| Cypermethrin | 50 | 3 | 4 | 13 |
| Sulfur spray granules | 500 | 58 | 60 | 43 |
| Cypermethrin in combination with sulfur spray granules | 50 500 | 72 | 82 | 72 |
| Untreated control | — | — | — | — |

5. Treatment of Broad Mites (*Polyphagotarsonemus latus*) in Chili
In the control of broad mites in chili crops, the following results were obtained:

|  |  | % activity (mortality) | |
| --- | --- | --- | --- |
| Treatment | g of a.i./ha | 3 days post-treatment | 7 days post-treatment |
| Cypermethrin | 50 | 68 | 68 |
| Sulfur spray granules | 500 | 58 | 71 |
| Cypermethrin in combination with sulfur spray granules | 50 500 | 75 | 80 |

6. Control of Spider Mites (*Tetranychus macfarlaner*) in Aubergines
Spider mite control in the aubergine crops was carried out in 2 treatments. The results were as follows:

|  | g of a.i./ha | Number of mites/3 leaves | | | | | |
| --- | --- | --- | --- | --- | --- | --- | --- |
|  |  | Treatment 1 | | | Treatment 2 | | |
|  |  | 1 DPT | 3 DPT | 7 DPT | 1 DPT | 3 DPT | 7 DPT |
| Cypermethrin | 50 | 208 | 230 | 247 | 104 | 100 | 127 |
| Sulfur spray granules | 500 | 166 | 70 | 86 | 90 | 61 | 69 |
| Cypermethrin + sulfur spray granules | 50 500 | 155 | 56 | 71 | 102 | 49 | 41 |
| Untreated control | — | 207 | 223 | 215 | 104 | 118 | 146 |

(DPT = days post-treatment)

We claim:

1. A pesticide comprising an active ingredient combination composed of
   a) sulfur melt spray granules or sulfur spray granules made from suspended sulfur, and
   b) a pyrethroid.

2. The pesticide defined in claim 1, wherein the pyrethroid is at least one compound selected from the group consisting of *permethrin, fenvalerate, esfenvalerate, cypermethrin, alphacypermethrin, deltamethrin, fenpropathrin, fluvalinate, flucythrinate, cyfluthrin, acrinathrin, tralomethrin, cycloprothrin, lambdacyhalothrin, tefluthrin, bifenthrin, transfluthrin, zeta-cypermethrin, fubfenprox and flufenprox.*

3. The pesticide defined in claim 1, which comprises 0.1 to 100% by weight of active ingredient combination.

4. The pesticide defined in claim 1, comprising the sulfur spray granules a) and the pyrethroid b) in a weight ratio of from 10000:1 to 2:1.

5. The pesticide defined in claim 1, wherein the active ingredient combination is obtained by mixing the sulfur spray granules with a pulverulent composition comprising the pyrethroid and an inert carrier.

6. The pesticide defined in claim 1, wherein the active ingredient combination is obtained by spraying the pyrethroid or a solution of the pyrethroid in an organic solvent onto the sulfur spray granules.

7. The pesticide defined in claim 1, wherein the active ingredient combination is obtained by spraying the pyrethroid or a solution of the pyrethroid in an organic solvent onto the sulfur spray granules together with additional adjuvants.

8. The pesticide defined in claim 1, wherein the active ingredient combination is obtained by spraying the pyrethroid in emulsion form onto the sulfur spray granules.

9. The pesticide defined in claim 1 further comprising an inert carrier.

10. A process for the preparation of the pesticide defined in claim 1, wherein a pulverulent composition comprising the pyrethroid and a carrier material, is applied to the sulfur spray granules.

11. The process defined in claim 10 wherein the pulverulent composition is obtained by spraying the pyrethroid or a solution of the pyrethroid in an organic solvent onto the carrier material.

12. A process for the preparation of the pesticide defined in claim 1, wherein the pyrethroid or a solution of the pyrethroid in an organic solvent, is sprayed onto the sulfur spray granules.

13. A process for the preparation of the pesticide defined in claim 1, wherein the pyrethroid in emulsion form is sprayed onto the sulfur spray granules.

14. A process for the preparation of the pesticide defined in claim 1, wherein a suspension of pulverulent sulfur and the pyrethroid is sprayed to give pyrethroid-comprising sulfur spray granules.

15. A method of controlling pests, which comprises treating the pests or the areas or spaces to be kept free from pests with a pesticidally active amount of the pesticide defined in claim 1.

16. The method of claim 15, wherein the pests are insects or arachnids.

17. The method of claim 15, wherein the pests are ectoparasites in veterinary medicine.

* * * * *